(12) United States Patent
Katz

(10) Patent No.: US 8,535,055 B2
(45) Date of Patent: Sep. 17, 2013

(54) METHOD AND KIT FOR PRODUCING DENTAL IMPLANT DRILLING GUIDES

(76) Inventor: Howard Ian Katz, La Jolla, CA (US)

( * ) Notice: Subject to any disclaimer, the term of this patent is extended or adjusted under 35 U.S.C. 154(b) by 279 days.

(21) Appl. No.: 13/183,386

(22) Filed: Jul. 14, 2011

(65) Prior Publication Data

US 2012/0251978 A1 Oct. 4, 2012

Related U.S. Application Data

(60) Provisional application No. 61/468,259, filed on Mar. 28, 2011, provisional application No. 61/507,945, filed on Jul. 14, 2011.

(51) Int. Cl.
*A61C 3/04* (2006.01)
*A61C 19/04* (2006.01)
*A61C 13/36* (2006.01)

(52) U.S. Cl.
USPC ............. 433/75; 433/72; 433/196; 433/215

(58) Field of Classification Search
USPC ............. 433/75, 76, 165, 172–176, 196, 72, 433/215; 606/96–98; 408/202, 241; 33/513–514
See application file for complete search history.

(56) References Cited

U.S. PATENT DOCUMENTS

| | | | | |
|---|---|---|---|---|
| 5,486,109 A | * | 1/1996 | Hunter et al. | 433/72 |
| 5,538,424 A | * | 7/1996 | Gelb | 433/72 |
| 5,556,278 A | * | 9/1996 | Meitner | 433/75 |
| 5,743,916 A | * | 4/1998 | Greenberg et al. | 606/102 |
| 5,989,025 A | * | 11/1999 | Conley | 433/76 |
| 6,099,313 A | * | 8/2000 | Dorken et al. | 433/175 |
| 7,097,451 B2 | | 8/2006 | Tang | |
| 2006/0257817 A1 | * | 11/2006 | Shelton | 433/75 |
| 2008/0064005 A1 | * | 3/2008 | Meitner | 433/74 |
| 2008/0176187 A1 | * | 7/2008 | Stumpel | 433/196 |

* cited by examiner

*Primary Examiner* — Todd Manahan
*Assistant Examiner* — Michael R Ballinger
(74) *Attorney, Agent, or Firm* — Stephen E. Zweig

(57) ABSTRACT

A method and kit for producing implant drilling guides positioned at the proper angle and orientation so as to avoid inadvertent damage to critical regions of the patient's jaw when drilling to place dental implant screws. The method works by placing a small post with x-ray visible depth markers in the root of the patient's tooth immediately after tooth extraction. This post, along with guideblocks, optional washers, reduction or expansion guides, and rapidly hardening guide materials (such as acrylics or thermosetting materials) is used to construct a removable guide that anchors to the patient's adjacent teeth, and preserves the location and orientation of the extracted tooth root. Once the root is filled in with new bone, the guide, in conjunction with the X-ray post depth information, can be used to direct drilling along the same route as the old tooth root, thus avoiding critical structures.

13 Claims, 11 Drawing Sheets

METHOD AND KIT FOR PRODUCING DENTAL IMPLANT DRILLING GUIDES

CROSS REFERENCE TO RELATED APPLICATIONS

This application claims the priority benefit of provisional patent application 61/468,259, "Device that records the exact spatial position, location in the jawbone, root socket depth and orientation of a recently extracted tooth that may be used to locate an ideal site to replace a tooth. It measures the location and dimensions of a tooth socket seconds after a tooth has been extracted before the socket has began to heal", inventor Howard Ian Katz, filed Mar. 28, 2011; this application also claims the priority benefit of provisional patent application 61/507,945, "METHOD AND KIT FOR PRODUCING DENTAL IMPLANT DRILLING GUIDES", inventor Howard Ian Katz, filed Jul. 14, 2011.

BACKGROUND OF THE INVENTION

1. Field of the Invention

This invention is in the field of dental implants and methods and kits to assist the dental implant process.

2. Description of the Related Art

Dental implants have become popular in recent years as a way to provide permanent artificial teeth to patients who have lost their original teeth and teeth roots. The basic concept is fairly simple. The dentist drills into the patient's jaw bone and implants an artificial tooth root, often made of titanium or other strong biocompatible material, which essentially resembles a small threaded screw. Natural bone, by a process called osseointegration, then fuses with this screw like artificial root. An artificial crown can then in turn be screwed into the artificial root, and to all intents and purposes, the dental implant then performs like a natural tooth.

If an adequate amount of natural bone remains after the extraction of the natural tooth root, then the implant process can commence soon after tooth extraction. However if, as is often the case, an inadequate amount of natural bone remains in the tooth socket after extraction of the natural root, the empty tooth socket may have to be first filled with artificial bone material. Over the course of a few months, the artificial bone filled empty socket will gradually fill in with new natural bone. The implant can then be drilled into this new natural bone.

In practice, installing implants is both complex and risky because there is little tolerance for error in the drilling step. The various bones of the jaw are often both very thin, and placed against other important structures. For example the bones of the upper jaw border on the delicate open sinus structures, and accidentally drilling into the sinus region is of course very bad. The bones of the lower jaw are also tricky to work with. In addition to the risk of the drill bit accidently extending outside the lower jaw bone, there are also various lower jaw structures, such nerve canals, blood vessels, and the like, where accidental drilling can cause substantial permanent damage to the patient.

As a result, general dentists who may be otherwise comfortable with other parts of the implant process, such as tooth extraction, filling up tooth sockets with artificial bone, and installing artificial crowns into previously installed implant roots, are often reluctant to do implant drilling. Instead, after tooth extraction, they will either fail to recommend an implant at all (and instead recommend a dental bridge), or alternatively send the patient to a specialist such as an oral surgeon or periodontist who will in turn do the drilling and implant.

Unfortunately, the general dentist is in a difficult conflict of interest situation here. This is because as a result of the implant referral, the general dentist will lose out on the subsequent implant revenue from that patient. Thus at present, implants, although they may give superior results, tend to be a bit underused.

Even oral surgeons and periodontists need specialized help to safely guide drilling, however. Here, to guide drilling, the present practice is to use computerized tomography and 3D materials fabrication technology (e.g. computer controlled steriolithography, CNC machining, and the like) to create a custom implant drilling guide. To do this, 3D image information on the structure of the patient's jaw, is used to determine the optimum drilling angle, and the computer controlled fabrication technology is then use to create a custom drilling guide. Such computerized tomography devices and 3D fabrication methods are very expensive, and as a result, implant guides alone can often cost around $1000 or more.

As another alternative, the dentist, oral surgeon, or peridontist can attempt to drill guided only by professional judgment and standard dental X-rays, and assume the risk of problems and complications that may result. However this is not a risk that most general dentists, or their insurance providers, usually wish to assume.

Alternative approaches include Tang, U.S. Pat. No. 7,097,451, who teaches a thermoplastic surgical template and method for performing dental implant osteotomies. Unfortunately Tang fails to suggest how such a template may be oriented properly with respect to critical structures in the patient's jaw.

As a result, there is a strong disconnect between the process of tooth extraction and the beginning of the implant process. Implants cross the discipline barriers between general dentistry and oral surgery/periodontry. This disconnect adds a substantial amount of expense to the dental implant process, and often results in patients being encouraged to adopt less optimal solutions, such as dental bridges.

BRIEF SUMMARY OF THE INVENTION

The present invention is based, in part, on the insight that the patient's natural tooth socket, and in particular the hole in the bone (root socket, extraction socket) left over when the patient's natural tooth root has been extracted, is often the perfect location to subsequently locate an implant screw, at least once this natural root socket has filled in with new bone. This is because natural tooth root, originally avoided any critical structures such as nerves, and was usually well positioned with respect to the other surrounding bone.

The present invention is also based, in part, on the insight that present practice, which typically determines the optimum angle for implant screw insertion days, weeks, or months after the natural tooth has been extracted, is suboptimum. Rather, the optimum time to determine the angle, depth, and location of the natural root socket is immediately after the natural tooth has been extracted.

In one embodiment, the invention is a method and kit for determining the angle, depth, and location of the natural root socket immediately after (or at least relatively soon after) extraction of the natural tooth. Once this angle, depth, and location information has been determined, the invention further provides a means to quickly produce an implant drilling guide that captures this information, and makes it available to guide subsequent implant drilling up to months and even years later. Thus once the original tooth socket has filled in with new bone, the record of the position and depth of the original tooth socket is well suited for the subsequent implant drilling procedure The invention's method and kit is designed to function using equipment typically available in general dentistry offices, such as standard X-ray equipment, and the like, and does not require use of sophisticated and expensive computerized tomography and computer controlled plastics fabrication equipment. The invention's method and kit is also designed to be simple enough to be operated by general dentists, although of course it may also be used by oral surgeons, peridontists, and other specialists as well.

Thus in one embodiment, the invention may be a method and kit for producing implant drilling guides positioned at the proper angle and orientation so as to avoid inadvertent damage to critical regions of the patient's jaw when drilling to place dental implant screws. The method works by placing a small post with x-ray visible depth markers in the root of the patient's tooth immediately after tooth extraction. This post, along with guideblocks, optional washers, reduction or expansion guides, and rapidly hardening guide materials (such as acrylics or thermosetting materials) is used to construct a removable guide that anchors to the patient's adjacent teeth, and preserves the location and orientation of the extracted tooth root. Once the root is filled in with new bone, the guide, in conjunction with the X-ray post depth information, can be used to direct drilling along the same route as the old tooth root, thus avoiding critical structures. Alternatively, in some situations, the guide may be used to direct drilling to certain regions of the jaw bone, such as the interradicular bone, where implants may be safely implanted before the roots of the extracted tooth fill in with new bone.

DETAILED DESCRIPTION OF THE INVENTION

In one embodiment, the invention may be a method of aligning a dental implant based upon the position and depth of the natural tooth socket at the time of tooth extraction. The invention may also be a kit of components to accomplish this method. The method will generally comprise or at least start by extracting a tooth from the jaw of a human patient. This patient will generally have a fair number of other teeth, usually including other teeth reasonably adjacent to the empty tooth socket left in the patient's jaw, after the tooth has been extracted.

According to the method, the practitioner will obtain a post (often made of a radioopaque material such as aluminum, and often generally cylindrical in configuration). This post will generally have length and width (e.g. diameter) dimensions that will allow the post to penetrate substantially to the bottom of the empty tooth socket (i.e. at or near the bottom of the tooth root socket). The practitioner will then position the post in the empty tooth socket.

Figure 1:
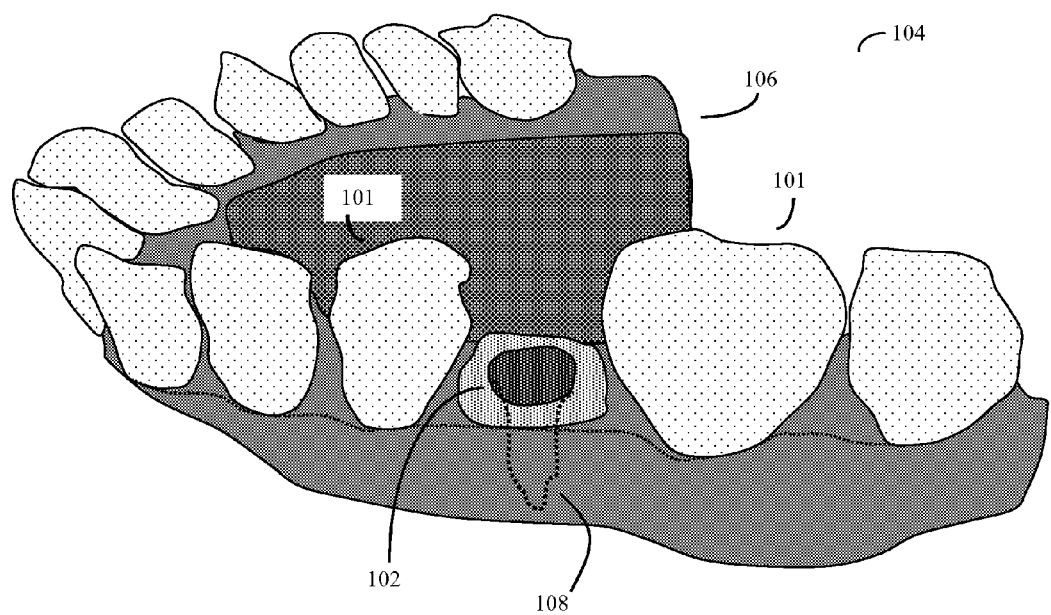
FIG. 1 shows the process of installing a post into the empty root socket of an extracted tooth.
Figure 1A:
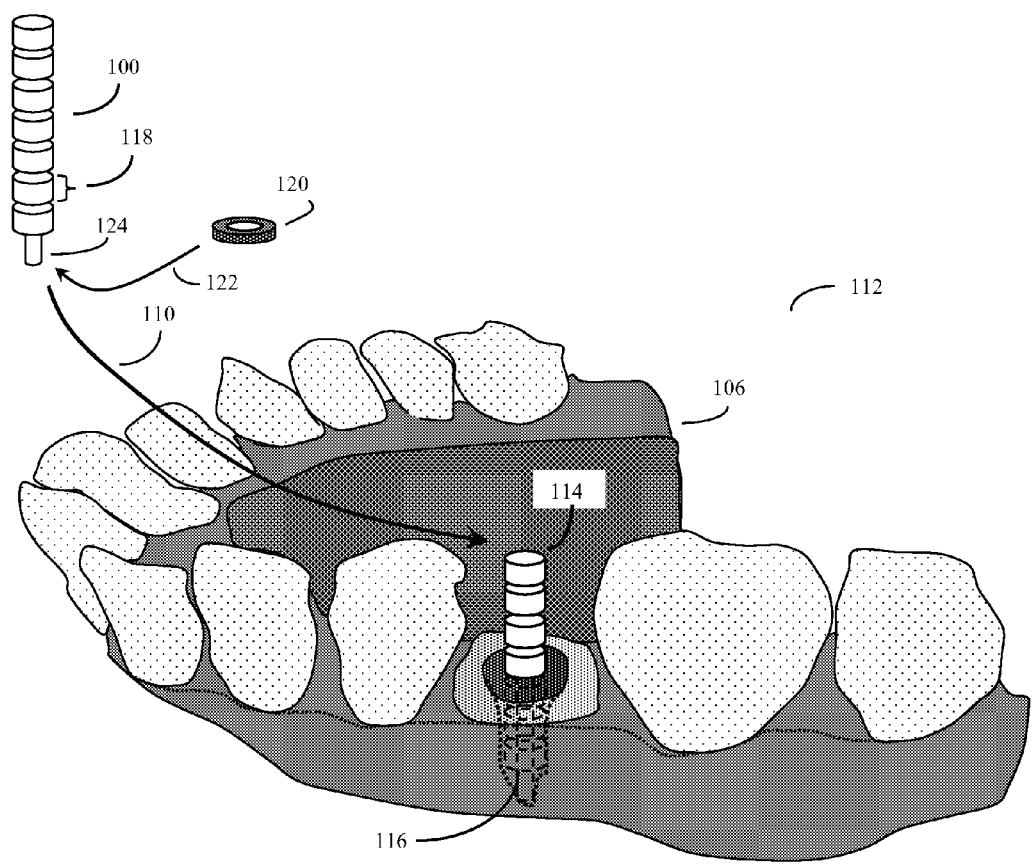

FIGS. 1 and 1A shows the process of installing a post (100) into the empty tooth socket (102) of an extracted tooth in the jaw of a patient (106). The jaw with the empty socket is shown as (104). In (108), the depth of the root portion (root socket) of the empty tooth socket (102) inside the jaw is shown by the dotted line, and the post (100) has not yet been inserted.

In (110), the post insertion process is shown by the arrow, producing a socket with a post inserted as shown in (112). The top part of the post (114) protrudes above the tooth socket, while the lower tip of the post (116) can be seen penetrating substantially towards the bottom of the empty root socket as dashed lines to signify that this part of the post is inside the patient's jawbone.

Some of the patient's teeth adjacent to the empty tooth socket are shown as (101). Here the term "adjacent" is used as a shorthand description for those teeth that are close enough to the empty tooth socket to usefully serve to anchor the implant guide (guide) and the guide material, which will be described shortly. Thus although in this example, teeth immediately on either side of the empty tooth socket (102) are shown, in other cases, the "adjacent" teeth may be further away from the empty tooth socket, and may not be located on either side of the empty tooth socket.

To help protect the empty tooth socket bony walls from damage due to the post, the practitioner may optionally place various small protective and somewhat flexible O-rings (often made from an elastic- or semi-elastic material) around various portions of the post. For example, a small diameter O-ring (120) may be placed (122) around the lower tip of the post (124) as needed.

To help determine how deep this root socket is, the post will usually have a number of X-ray visible markers, such as detents or grooves (118), positioned along the length of the post. Thus the dentist or other practitioner can, after inserting the post, take standard dental X-ray images of the post, and by counting grooves (118) or other X-ray visible markers determine the depth of the natural root socket, and this information in turn can be used later to guide the implant drilling process. The X-ray process will be shown in more detail later in FIGS. 3 and 3A.

Figure 2:
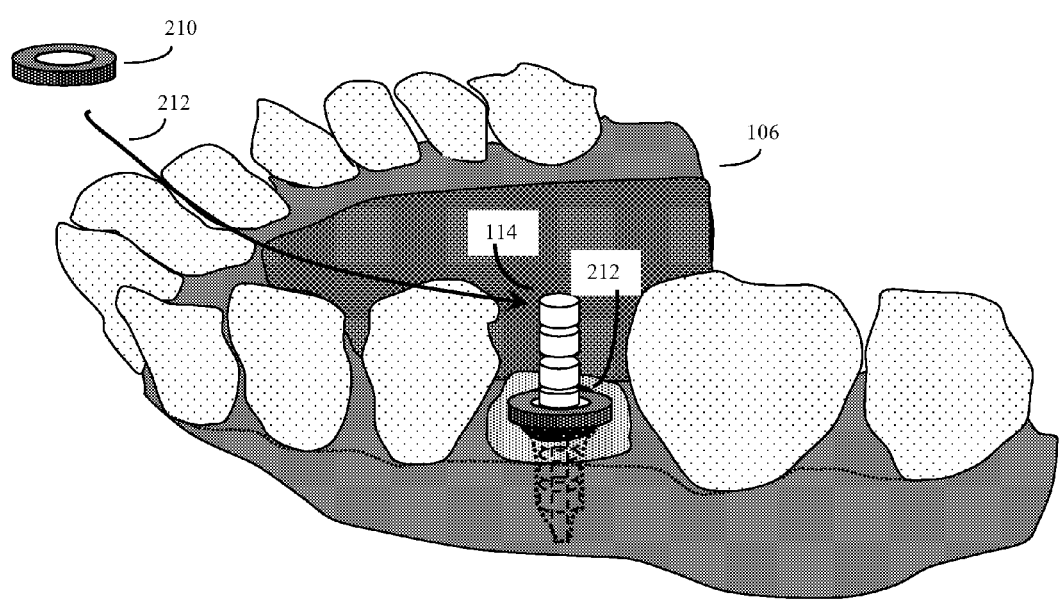
FIG. 2 shows the process of installing an optional O-ring, followed by placement of a guideblock with one hole over the post.
Figure 2A:
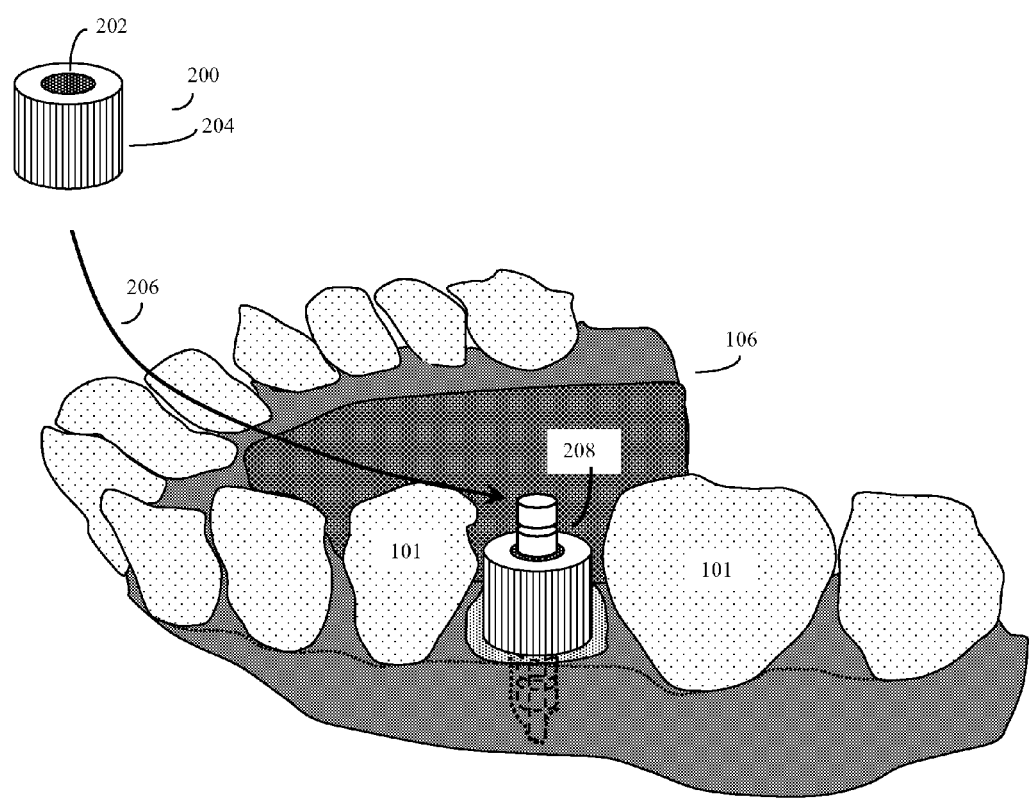
FIG. 2A shows the further process of installing an optional O-ring, followed by placement of a guideblock with one hole over the post.

As shown in FIGS. 2 and 2A, the practitioner will then obtain a guideblock (200), which often will be a hollow cylinder with one or more interior openings (202) intended to allow the post (100), (114) to pass through the guideblock. More specifically, the guideblock will have an outer surface (204) which is often textured or knurled in order to better adhere to the guide material (to be discussed), and at least one hole (202), this at least one hole having dimensions capable of fitting over at least a portion (e.g. the top portion) of the post (100).

The practitioner will then stabilize the post, while the post is still inserted in the empty tooth socket, by slipping the guideblock over the post (206), so that the top part of the post (100), (114) goes through one of the guideblock's holes (202), (208). Optionally, before the guideblock (200) is slipped over the post (100), (114), one or more additional semi-elastic O-rings (210) may be used (212) to help further stabilize the post (100), (114). Thus, for example, after the post is inserted into the socket, optionally an O-ring (210) may be placed on top of the post (114), followed by the guideblock (200), optionally followed by another O-ring as needed (not shown).

Figure 3:
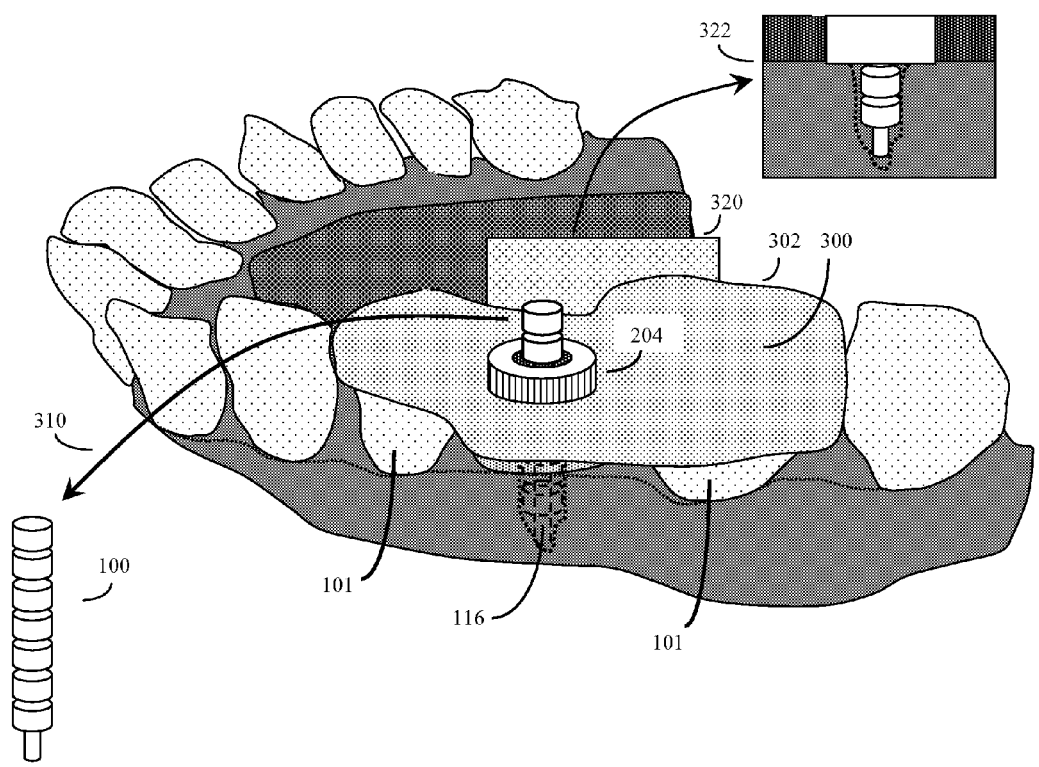
FIG. 3 shows the process of molding a flexible rapidly hardening guide material over the guideblock, as well as over other teeth adjacent to the extracted tooth, followed by a dental X-ray to determine the depth of the post. After the guide material has hardened, the post and guide may be removed, and the guide stored for later use during the implant procedure. For some procedures, the empty tooth socket may then be filled with artificial bone. New bone will then fill the empty socket by a process of osseointegration.
Figure 3A:
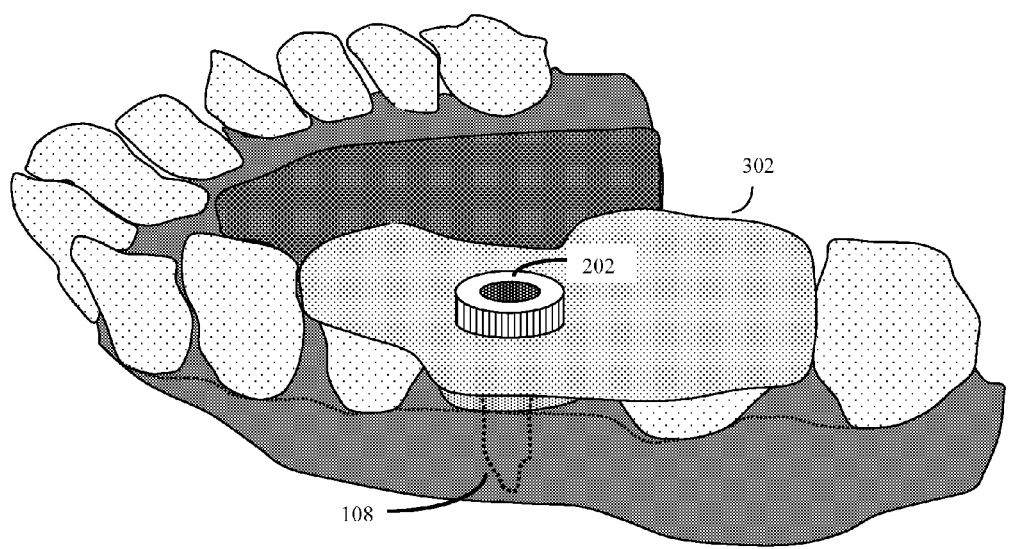
FIG. 3A shows the further process of molding a flexible rapidly hardening guide material over the guideblock, as well as over other teeth adjacent to the extracted tooth, followed by a dental X-ray to determine the depth of the post. After the guide material has hardened, the post and guide may be removed, and the guide stored for later use during the implant procedure. For some procedures, the empty tooth socket may then be filled with artificial bone. New bone will then fill the empty socket by a process of osseointegration.

As shown in FIGS. 3 and 3A, the practitioner will then in turn both stabilize the position of the guideblock relative to the position of at least some of the patient's other teeth (101) adjacent to the empty tooth socket (102) by using a flexible but rapidly hardening material, such as an acrylic or thermoplastic guide material (300), to construct a guide (302) that contacts at least some of the outer surface (204) of the guideblock (200) and the outer surface of at least some of the adjacent teeth (101). Usually the dentist will work quickly to build up the guide while the guide material (302) is flexible and optionally self-adhesive, and then allow the guide to harden while it is in the patient's mouth. Thus the guide (302), after it has hardened and is rigid, locks the guideblock (200) into position relative to the patient's adjacent teeth (101), and the hole or holes in the guideblock (202) in turn preserve the position and orientation of the post (100), which in turn preserves the position and orientation of the patient's natural tooth root (108).

Usually when the guide has hardened, but optionally also at other stages in the process, the practitioner will also take standard dental X-rays, or other X-rays as desired (320, 322), to determine the depth of the post (100) in the empty tooth socket (108). This can be used later to determine a safe drilling depth for the dental implant. As an example, X-ray film or a solid state X-ray detector (320) can be placed inside the patients mouth near the post, exposed with X-rays from outside the mouth (not shown), and the film or X-ray detector, when analyzed (322) will show the relative depth of the post in the root socket. This information will be preserved for the subsequent drilling step.

When the guide material has hardened, the practitioner can then remove the post (310) from the empty tooth socket (102), (108) and guideblock (200). The guide itself (302), which incorporates the guideblock (200) can then be saved and when the patient is ready (for example when the tooth socket (102) is fully filled in with new bone and is now ready), the guide (302) can be repositioned over the patent's adjacent teeth (101). The hole in the guideblock (202) will preserve the location and angle of the original tooth root (108), and the depth information of the post (100), as determined by inspection of X-rays taken when the post was inserted (322), can tell the practitioner how far in to drill when placing and aligning the dental implant.

Implant screws (artificial roots) come in a variety of different diameters, and often it is not feasible to predict in advance what diameter drill will be needed to create a hole for a particular brand or type of implant screw. As a result, often it will be more practical to make the guide hole (202) or holes somewhat larger, and to use an optional drill reduction guide (400) to reduce the diameter of the drill hole to more precisely control the orientation of a smaller diameter drill bit used to drill the implant hole.

Figure 4:
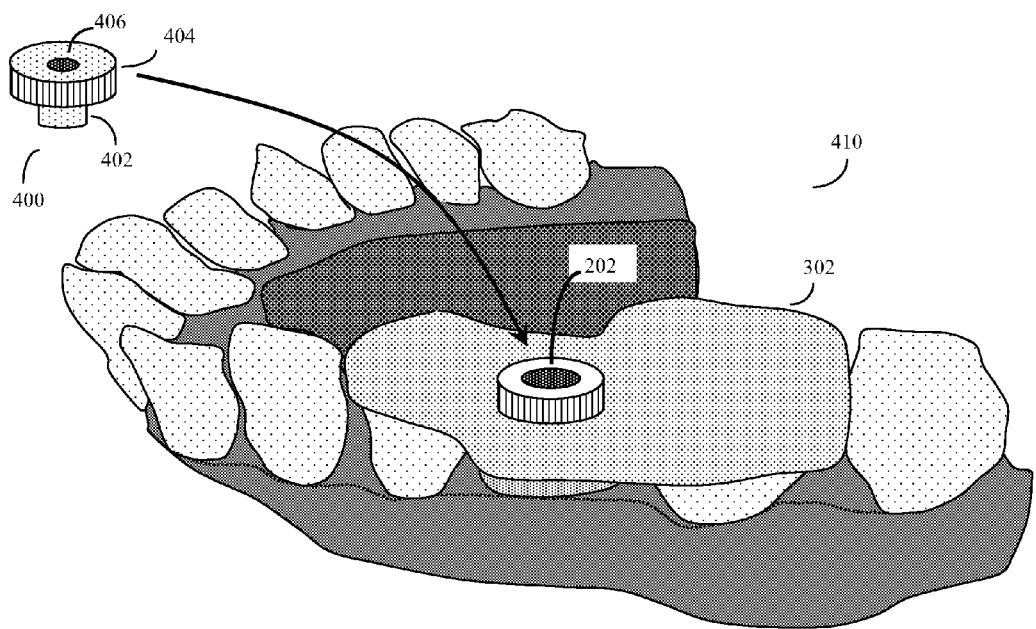
FIG. 4 shows how the implant guide, along with an optional drill reduction guide, can be used, along with optional post depth information from the dental X-ray from FIG. 3, to ensure that the implant drilling process proceeds in the "safe" area of the jaw that was generally occupied by the original tooth root.
Figure 4A:
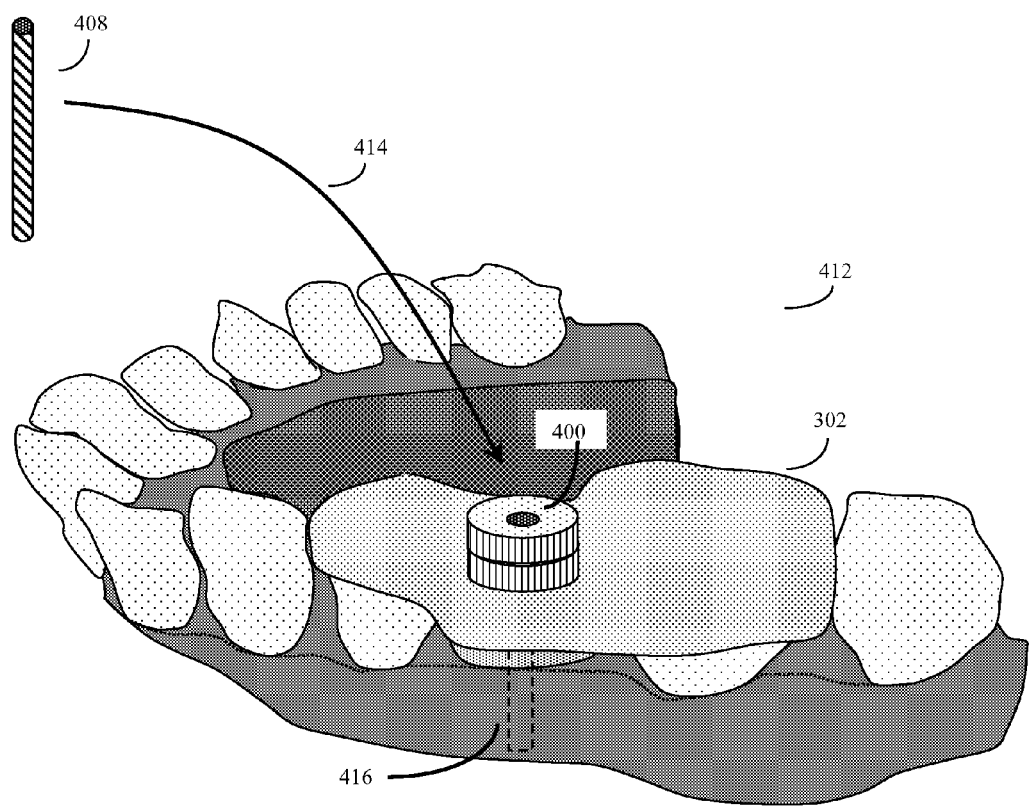
FIG. 4A shows further how the implant guide, along with an optional drill reduction guide, can be used, along with optional post depth information from the dental X-ray from FIG. 3, to ensure that the implant drilling process proceeds in the "safe" area of the jaw that was generally occupied by the original tooth root.

FIGS. 4 and 4A shows how the implant guide (302), along with an optional drill reduction guide (400), can be used, along with optional post depth information from the dental X-ray (322) previously discussed in FIGS. 3 and 3A, to ensure that the implant drilling process proceeds in the "safe" area of the jaw that was generally occupied by the original tooth root (108), or in other safe spot such as the interradicular bone between the roots of a multiple root molar or other type tooth.

The drill reduction guide, also called a drill reduction guidance sleeve, is often an approximately cylindrical device. The outer diameter of the cylindrical portion of the drill reduction guidance sleeve (402) will usually have dimensions configured to enable it to fit snugly but reversibly inside the diameter of hole (202), and the outer diameter of the flange (404) may have dimensions configured so that the flange is substantially the same diameter as guideblock (200). The hole or holes (406) of the drill reduction guidance sleeve will be dimensioned as best to accommodate the particular implant drill (408) of choice for that particular tooth and implant design.

In FIG. 4 (410), the dotted line showing the tooth root socket, previously shown as (108), has been removed to symbolize that often, this step of the procedure will be done after the tooth socket (102) and root socket (108) have been filled with artificial bone, and allowed to heal, thus filling the space occupied by the original root socket (108) with new bone (e.g. new natural bone growing to occupy the space occupied by the artificial bone material). Although this former root socket is now filled in with new bone, it still represents a very safe place to drill (108) to put the implant screw in. In FIG. 4A, just the implant drill bit is shown, and the drill (usually an electric or pneumatic drill) that turns the drill bit is not shown.

Thus, usually by way of a motorized drill, drill bit (408) will be used, often in conjunction with an optional reduction sleeve or tool to drill a hole in the jaw at safe location as determined by guide (302). This is shown in FIG. 4A (412). Drill bit (408) drills (414) through the hole(s) in the optional guidance sleeve (400) or tool, and the guideblock (200), and produces an opening (dashed lines) (416) for an implant screw that is located in a known safe location (the previous root socket location) in the patient's jaw.

Alternatively, a plurality of different sized (different hole size (406)) drill reduction guides (400) can instead be mounted onto a tool that contains a plurality of drill reduction guides positioned on a handle. Here again, the drill reduction guides can be configured to fit in the at least one hole(s) (202) of the guideblock (200), and further constrain the diameter of this at least one hole (202) to approximately the diameter of a drill bit (408) for an implant of choice. This tool can be useful because it can facilitate rapid selection among different implant drill bit sizes (408) and different implant screw diameters.

Some teeth near the back of the jaw, such as molars, have multiple roots. The bone between these roots is called the interradicular bone. In some cases, this interradicular bone may be large enough and well developed enough so as to directly serve to hold the implant screw even before the root sockets of the extracted molar have been filled in with artificial bone and allowed to heal. Alternatively, even after the original root sockets have filled in with fresh bone, the interradicular bone may still be the preferred place to plant the implant screw. In this type of situation, a variant of the invention may be used.

Figure 5:
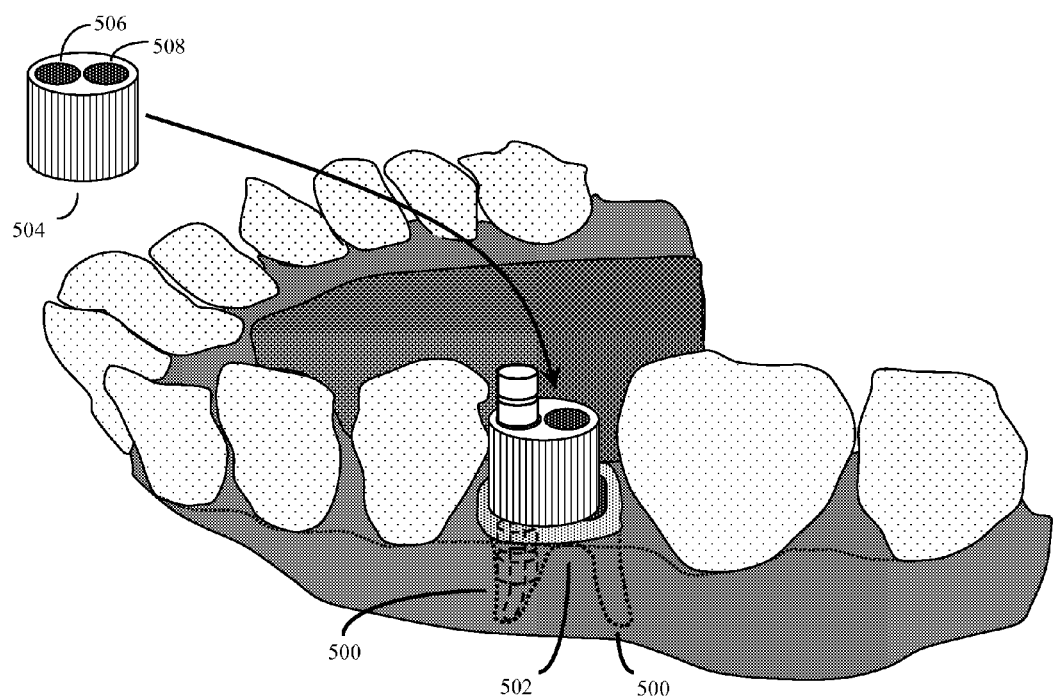
FIG. 5 shows a variant of this process for a multiple root tooth, such as a molar. Here the post is placed down the root socket of one of the roots, and a two-hole guideblock is used. Here the second hole in the guideblock is used to guide implant drilling into the interradicular bone between the roots of the multiple root tooth for extra implant strength.
Figure 5A:
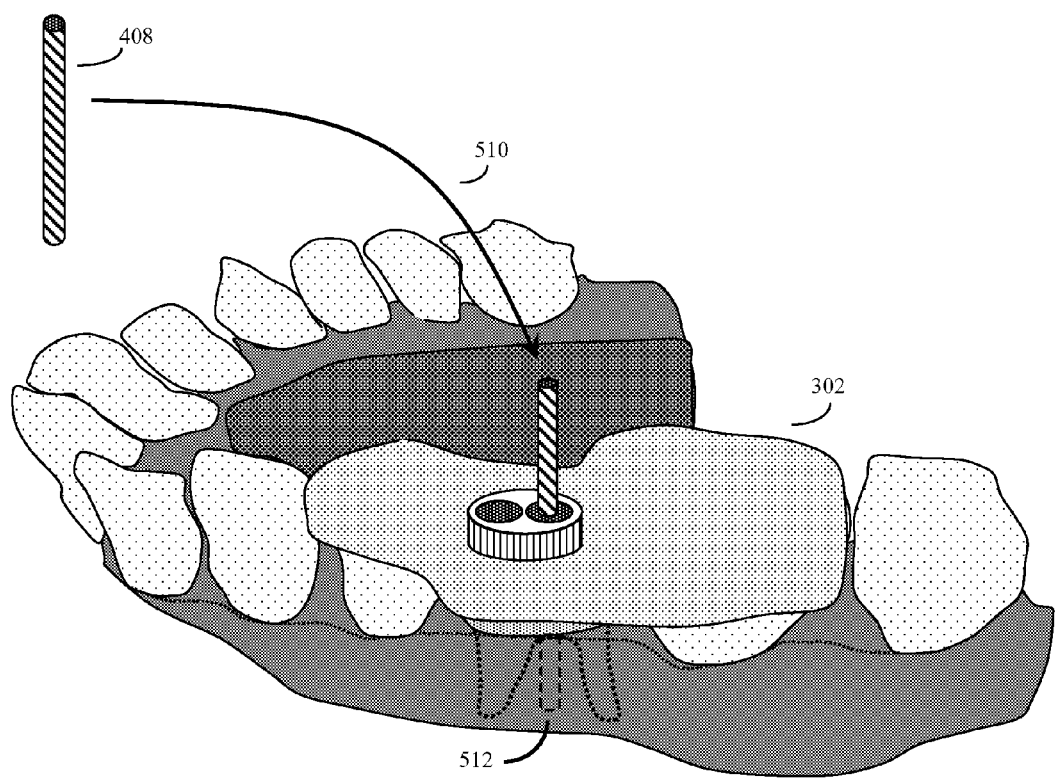
FIG. 5A further shows a variant of this process for a multiple root tooth, such as a molar. Here the post is placed down the root socket of one of the roots, and a two-hole guideblock is used. Here the second hole in the guideblock is used to guide implant drilling into the interradicular bone between the roots of the multiple root tooth for extra implant strength.

FIGS. 5 and 5A shows a variant of this process for a multiple root tooth, such as a molar. The two root sockets corresponding to the extracted molar (molar tooth socket) are shown in dotted lines as (500), and the interradicular bone between the two molar root sockets is shown as (502).

Here the post (100) is placed down the root socket of one of the roots, and a two-hole guideblock (504) is used. Here the first hole in the guideblock (506) may be used to position the post (100), while the second hole (508) in the guideblock may be used to guide implant drilling into the interradicular bone (502) between the roots (500) of the multiple root tooth.

Thus the post (100) is placed into one empty root socket, and this post is used with hole (506) to position the orientation of two-hole guideblock (504) in the context of guide (302). Hole (508) is then subsequently used to position a drilling procedure (408), (510) for a dental implant into the interradicular bone between the roots of the molar. Again, the hole for the implant (512) ends up in a safe place on the jaw, in this case in the interradicular bone (502).

Figure 6:
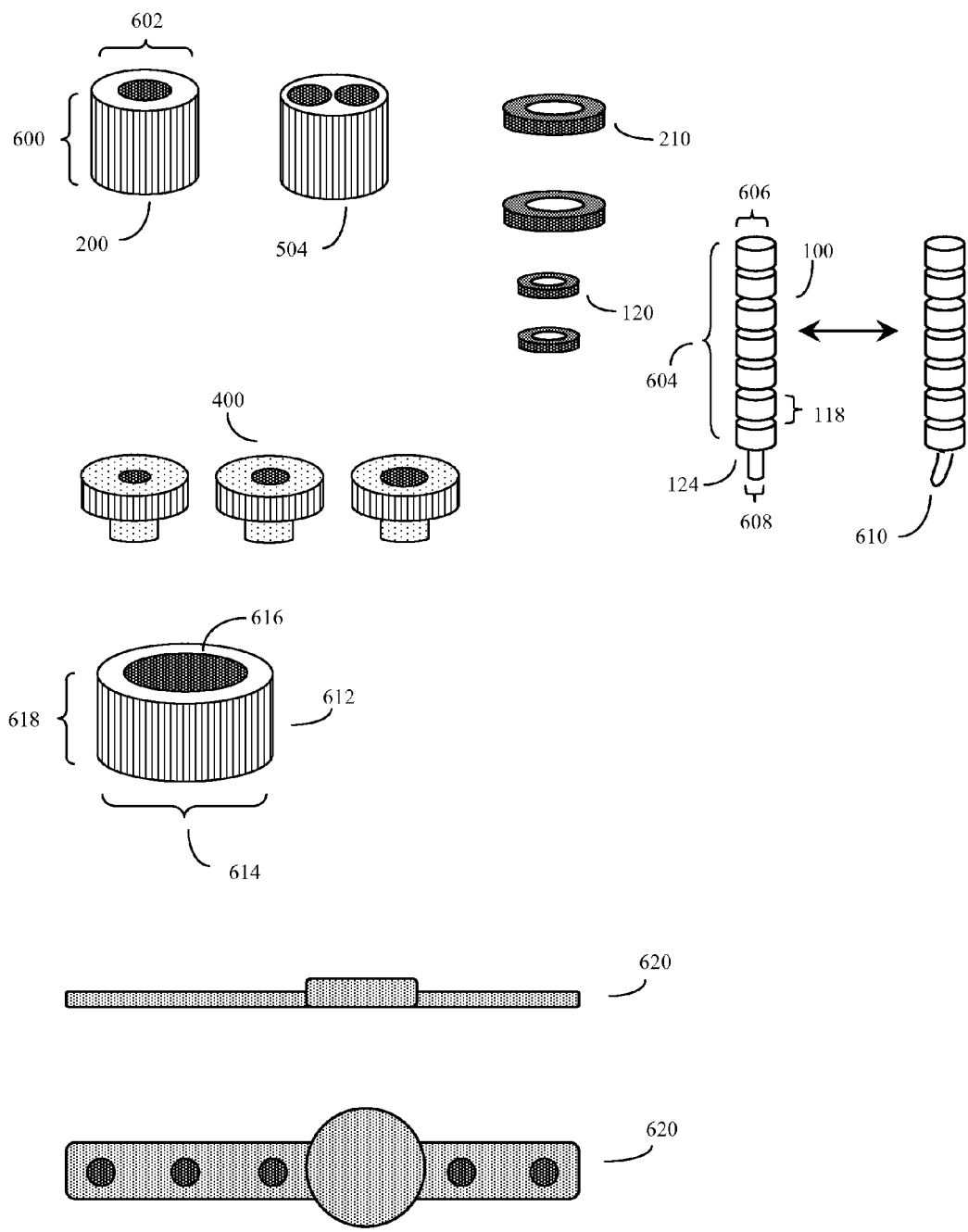
FIG. 6 shows an example of some of the components, such as the post, various guideblocks, washers, optional reduction guides and/or expansion guides, and optional guide material and instructions (not shown) that may be provided in a kit form of the invention.

FIG. 6 shows an example of some of the components, such as the post (100), various guideblocks (200), (504), washers (120), (210), optional reduction guides (400) and/or expansion guides (600), and optional guide material and instructions (not shown) that may be provided in a kit form of the invention. The washers will often be made from a semi-elastic rubber, plastic, or silicon like material, and may be designed both to help the post get a better fit into the tooth socket, as well as reduce trauma to the bone lining the tooth socket.

Often the height (600) of the guideblock (200), (504) will be such as to be somewhat shorter than that of the adjacent teeth (101). Here a value of around 7 mm, such as between 5 mm and 9 mm, is preferred, although this may vary somewhat according to the height of the adjacent teeth (101). The outer diameter (602) of the guideblock (200), (504) is often between 3 mm and 6 mm, although this will also vary somewhat with the size of the patient's teeth and the shape of the patient's mouth. Here the criteria is that the guideblock should fit between the nearest adjacent teeth to the tooth socket.

The guideblock holes (202), (506), (508) will generally be substantially cylindrical, and the inner diameter of the holes will generally be between 2 mm and 6 mm. The guideblocks themselves may be made of a tough metal, such as stainless steel, so as to better help hold up to minor drill bit misalignment during the drilling process.

The post (100) will generally have an overall shape substantially similar to that of a larger cylinder (604) with a diameter (606) often between about 2 mm and 4 mm. Post (100) will often have a smaller diameter cylindrical tip (124) attached along the axis of rotation of the larger cylinder (604). The diameter (608) of this smaller diameter cylindrical tip (124) is between 1 mm and 2 mm. As previously discussed, post (108) will frequently be made from a radio-opaque material, which may be chosen to be bendable (such as aluminum), and will often have X-ray visible markers (118), such as a plurality of grooves in the post, often with a spacing of about approximately 2 to 4 mm between grooves so as to show up clearly in a dental X-ray.

In some embodiments, at least the tip (124) of the post (100) is bendable (at least by way of dental instruments such as pliers and the like) and at least the tip of the post may be bent by the dentist or other practitioner in order to better fit the natural curvature of an empty tooth socket (108), (500). In some embodiments, the entire length of the post may be bendable, at least by the use of hand tools such as pliers. This bent post is shown in FIG. 6 as (610).

In some embodiments, instead of narrowing the diameter of a guideblock hole (202), (506), (508) using a reduction guide or sleeve (400), the practitioner may instead elect to first start with a smaller diameter (602) guideblock (200), (504), and elect to widen the diameter of the guideblock by slipping an expansion sleeve (612) over the guideblock (200), (505) before adding the guide material (300) and creating the implant guide (302). This process will proceed much as shown in FIGS. 2 and 2A, except that once the guideblock (200) is in position, expansion sleeve (612) will then be slipped over the guideblock (200). The diameter of the expansion sleeve will often be a few millimeters wider than that of the underlying guideblock, and the diameter of the inner hole (616) of the expansion sleeve will be designed to precisely fit the underlying guideblock. The walls of the expansion sleeve will also be textured or knurled to better grip on to the guide material (300). The expansion sleeve is designed to allow the dentist or other practitioner to use relatively wide drills, such as 5.5 mm diameter drills.

Thus, for example, if the guideblock has an outer diameter of 5.5 mm, then the expansion sleeve will have a central hole (616) only slightly larger than this, and an outer diameter (614) of around 7-8 mm.

As previously discussed, often it will be convenient to present some or all of the various devices shown in FIG. 6 as a kit for constructing a guide to align a dental implant based upon the position and depth of a natural tooth socket at the time of tooth extraction. Thus this kit may comprise, for example, at least one post (100) with length and width dimensions capable of penetrating substantially to the bottom of an empty tooth socket, a guideblock, one or more O-rings, one or more reduction or expansion sleeves, and the like. Other kit components, such as rapid hardening guide material (e.g. acrylic, thermoplastic material), instructions for use, reduction tools and the like, may also be provided.

In some embodiments, rather than having a plurality of different individual expansion sleeves (400), it may be convenient to provide a single tool (shown in top and side views as (620 and 622) that have a plurality of expansion sleeves built into it. This tool may optionally be provided as part of the kit as well.

In yet another alternative embodiment, post (100) and guideblock hole (202), (506) or (508) may have complementary screw threads. This complementary screw thread arrangement may be useful to further reduce movement of the guide relative to the post during the procedure.

The invention claimed is:

1. A method of aligning a dental implant based upon the position and depth of the natural tooth socket at the time of tooth extraction, said method comprising:

extracting a tooth from the jaw of a human patient having a plurality of other teeth, thus producing an empty tooth socket in said jaw;

obtaining a post with length and width dimensions capable of penetrating substantially to the bottom of said empty tooth socket, said post having a plurality of X-ray visible markers positioned along the length of said post, thus enabling the depth of said post in said tooth socket to be determined by dental X-ray images;

positioning said post in said empty tooth socket;

obtaining a guideblock with an outer surface and at least one hole, said at least one hole having dimensions capable of fitting over at least a portion of said post;

stabilizing said post by slipping one of said at least one hole of said guideblock over said post;

stabilizing the position of said guideblock, relative to the position of at least some of said plurality of other teeth that are adjacent to said empty tooth socket, by constructing a guide that contacts at least some of the outer surface of said guideblock and the outer surface of at least some of said plurality of other teeth using a rapid setting or thermoplastic guide material, so that when said guide material has hardened, the position of at least some of said plurality of other teeth and said guide act to hold said guideblock into a fixed position;

removing said post from said empty tooth socket and said guideblock; and using at least one hole in said guideblock to subsequently position a drilling procedure to install and align a dental implant.

2. The method of claim 1, wherein said guideblock is substantially cylindrical, and wherein at least the cylindrical outer side of said guideblock is knurled or otherwise textured so as to create a more secure connection with said guide material.

3. The method of claim 2, wherein the height of said guideblock is between 5 mm and 9 mm, and the outer diameter of said guideblock is between 3 mm and 6 mm.

4. The method of claim 2, wherein said at least one holes are substantially cylindrical, and wherein the inner diameter of said at least one holes are between 2 mm and 6 mm.

5. The method of claim 2, further positioning the cylindrical portion of an approximately cylindrical flanged drill reduction guidance sleeve inside said at least one hole of said guideblock, the outer diameter of said cylindrical portion of said drill reduction guidance sleeve being configured to fit snugly but reversibly inside the diameter of said at least one hole, and the outer diameter of said flange being configured so that said flange is substantially the same diameter of said guideblock.

6. The method of claim 2, wherein the position of a drill used to perform said drilling procedure is further stabilized by use of a tool that contains a plurality of drill reduction guides positioned on a handle, said drill reduction guides configured to fit in said at least one hole of said guideblock, and further constrain the diameter of said at least one hole to approximately the diameter of a drill bit for an implant of choice, thereby facilitating rapid selection among different implant drill bit sizes and different implant diameters.

7. The method of claim 1, wherein said post has a shape substantially similar to that of a larger cylinder, with a smaller diameter cylindrical tip attached along the axis of rotation of said larger cylinder;

and wherein the diameter of said larger cylinder is between 2 mm and 4 mm, and the diameter of said smaller diameter cylindrical tip is between 1 mm and 2 mm.

8. The method of claim 7, wherein said post is made from a radio-opaque material, and said X-ray visible markers comprise a plurality of grooves in said post with a spacing of approximately 2 to 4 mm between said grooves.

9. The method of claim 7, wherein at least the tip of said post is bendable, wherein at least said tip of said post is bent in order to better fit the natural curvature of said empty tooth socket.

10. The method of claim 1, wherein the position of said post in said tooth socket or guideblock is further stabilized by at least one O-ring.

11. The method of claim 1, further using information on the depth of said post in said tooth socket, as obtained from dental X-ray images showing said plurality of X-ray visible markers positioned along said post, to determine the depth of said drilling procedure.

12. The method of claim 1, wherein after said guide is constructed, further filling said empty socket with bone grafting material or synthetic bone material, and allowing said empty socket to heal prior to using said guideblock to subsequently position a drilling procedure for a dental implant.

13. The method of claim 1, wherein said post is used on a molar or other tooth with more than one root, and interradicular bone between said more than one root;

wherein said guideblock has at least two holes;

wherein said post is placed in one guideblock hole in the position corresponding to one root of said molar or other tooth, and a different guideblock hole is used to position a drilling procedure for a dental implant into the interradicular bone between the roots of said molar or other tooth.

* * * * *